US012797019B2

(12) United States Patent
Lu et al.

(10) Patent No.: US 12,797,019 B2
(45) Date of Patent: Nov. 17, 2026

(54) SYSTEMS AND METHODS FOR POSITRON EMISSION TOMOGRAPHY IMAGING

(71) Applicant: SHANGHAI UNITED IMAGING HEALTHCARE CO., LTD., Shanghai (CN)

(72) Inventors: Yihuan Lu, Shanghai (CN); Yue Li, Shanghai (CN); Hao Liu, Shanghai (CN); Chen Sun, Shanghai (CN); Duo Zhang, Shanghai (CN); Yun Dong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/950,237

(22) Filed: Nov. 18, 2024

(65) Prior Publication Data

US 2025/0072846 A1 Mar. 6, 2025

Related U.S. Application Data

(63) Continuation of application No. PCT/CN2023/114452, filed on Aug. 23, 2023.

(51) Int. Cl.
*A61B 6/03* (2006.01)
*A61B 6/00* (2024.01)

(52) U.S. Cl.
CPC ............ *A61B 6/037* (2013.01); *A61B 6/5205* (2013.01); *A61B 6/5264* (2013.01)

(58) Field of Classification Search
None
See application file for complete search history.

(56) References Cited

U.S. PATENT DOCUMENTS

| | | | |
|---|---|---|---|
| 10,292,671 | B2 | 5/2019 | Sanders et al. |
| 2010/0239134 | A1 | 9/2010 | Koehler et al. |

(Continued)

FOREIGN PATENT DOCUMENTS

| | | | |
|---|---|---|---|
| CN | 107137107 | A | 9/2017 |
| CN | 108921777 | A | 11/2018 |

(Continued)

OTHER PUBLICATIONS

Wang, Jizhe et al., Automatic Mismatch Correction and Motion Compensation for Free-breathing PET/CT, 2018 IEEE, 2018, 5 pages.

(Continued)

*Primary Examiner* — Christopher Koharski
*Assistant Examiner* — Farouk A Bruce
(74) *Attorney, Agent, or Firm* — METIS IP LLC

(57) ABSTRACT

A method and a system for PET imaging may be provided. PET data of a subject collected by a PET scan of the subject and a physiological signal relating to a physiological motion of the subject during the PET scan may be obtained. Gated PET images corresponding to physiological phases of the subject may be generated based on the PET data and the physiological signal. Further, for each physiological phase, a first attenuation map of the subject corresponding to the physiological phase may be generated based on the gated PET image corresponding to the physiological phase, and an attenuation corrected gated PET image corresponding to the physiological phase may be generated based on the first attenuation map and a portion of the PET data corresponding to the physiological phase. A target PET image corresponding to a reference physiological phase may be generated based on the attenuation corrected gated PET images.

17 Claims, 5 Drawing Sheets

(56) References Cited

U.S. PATENT DOCUMENTS

| | | | |
|---|---|---|---|
| 2013/0320973 A1 | 12/2013 | Fenchel et al. | |
| 2014/0072194 A1 | 3/2014 | Hansis et al. | |
| 2014/0153806 A1 | 6/2014 | Glielmi et al. | |
| 2015/0289832 A1 * | 10/2015 | Bal | A61B 5/055 600/407 |
| 2020/0008770 A1 * | 1/2020 | Salomon | G06T 7/20 |
| 2020/0134886 A1 | 4/2020 | Tsui et al. | |
| 2020/0393579 A1 | 12/2020 | Feng et al. | |
| 2021/0065412 A1 * | 3/2021 | Feng | G06T 11/005 |
| 2023/0009528 A1 * | 1/2023 | Schaefferkoetter | A61B 6/037 |
| 2023/0401769 A1 * | 12/2023 | Bharkhada | A61B 6/5205 |

FOREIGN PATENT DOCUMENTS

| | | | |
|---|---|---|---|
| CN | 110992280 A | 4/2020 | |
| CN | 111312373 A | 6/2020 | |
| CN | 108553121 B * | 5/2021 | A61B 6/037 |
| CN | 115049752 A | 9/2022 | |

OTHER PUBLICATIONS

F Lamare et al., PET respiratory motion correction: quo vadis?, Physics in Medicine & Biology, 67(3): 1-27, 2022.

Lee, Jae Sung, A Review of Deep-Learning-Based Approaches for Attenuation Correction in Positron Emission Tomography, IEEE Transactions on Radiation and Plasma Medical Sciences, 5(2): 160-184, 2021.

International Search Report in PCT/CN2023/114452 mailed on Dec. 21, 2023, 4 pages.

Written Opinion in PCT/CN2023/114452 mailed on Dec. 21, 2023, 4 pages.

The Extended European Search Report in European Application No. 23809956.8 mailed on Apr. 5, 2024, 10 pages.

* cited by examiner

SYSTEMS AND METHODS FOR POSITRON EMISSION TOMOGRAPHY IMAGING

CROSS-REFERENCE TO RELATED APPLICATIONS

This application is a continuation of International Application No. PCT/CN2023/114452, filed on Aug. 23, 2023, the contents of which is hereby incorporated by reference.

TECHNICAL FIELD

The present disclosure relates to medical imaging technology, and in particular, to systems and methods for positron emission tomography (PET) imaging.

BACKGROUND

PET imaging has been widely used in clinical examination and disease diagnosis in recent years. During a PET scan of a scanned subject, a physiological motion of the scanned subject may cause motion artifacts in a resulting image of the PET scan. Therefore, physiological motion correction is vital for PET imaging.

SUMMARY

According room an aspect of the present disclosure, a system for positron emission tomography (PET) imaging may be provided. The system may include at least one storage device including a set of instructions and at least one processor in communication with the at least one storage device. When executing the set of instructions, the at least one processor may be configured to direct the system to perform the following operations. The system may obtain PET data of a subject collected by a PET scan of the subject and a physiological signal relating to a physiological motion of the subject during the PET scan. The system also may generate a plurality of gated PET images corresponding to a plurality of physiological phases of the subject based on the PET data and the physiological signal. For each of the plurality of physiological phases, the system may generate a first attenuation map of the subject corresponding to the physiological phase based on the gated PET image corresponding to the physiological phase. Further, for each of the plurality of physiological phases, the system may generate an attenuation corrected gated PET image corresponding to the physiological phase based on the first attenuation map and a portion of the PET data corresponding to the physiological phase. Then, the system may generate a target PET image corresponding to a reference physiological phase among the plurality of physiological phases based on the attenuation corrected gated PET images corresponding to the plurality of physiological phases.

In some embodiments, to obtain a physiological signal relating to a physiological motion of the subject during the PET scan, the system may determine a target region of the subject that is affected by the physiological motion of the subject. The system may also determine a time activity curve (TAC) corresponding to the target region based on the PET data. Further, the system may generate the physiological signal of the subject based on the TAC.

In some embodiments, to obtain a physiological signal relating to a physiological motion of the subject during the PET scan, the system may determine a target region that is affected by the physiological motion of the subject. For each of time points during the PET scan, the system may determine a centroid of distribution (COD) of coincidence events in the target region at the time point based on the PET data. Further, the system may generate the physiological signal of the subject based on the COD corresponding to each of the time points.

In some embodiments, the for each of the plurality of physiological phases, to generate a first attenuation map of the subject corresponding to the physiological phase based on the gated PET image corresponding to the physiological phase, the system may perform the following operations. For each of the plurality of physiological phases, the system may generate the first attenuation map of the subject corresponding to the physiological phase by processing the gated PET image corresponding to the physiological phase using an attenuation map generation model. The attenuation map generation model may be a trained machine learning model.

In some embodiments, the attenuation map generation model may be generated according to a model training process. The system may obtain a plurality of training samples each of which includes a sample gated PET image and a ground truth attenuation map of a sample subject. The sample gated PET image and the ground truth attenuation map may correspond to the same physiological phase of the sample subject. Further, the system may generate the attenuation map generation model by training a preliminary model using the plurality of training samples.

In some embodiments, to generate a target PET image corresponding to a reference physiological phase among the plurality of physiological phases based on the attenuation corrected gated PET images corresponding to the plurality of physiological phases. The system may determine a first attenuation corrected gated PET image corresponding to the reference physiological phase and one or more second attenuation corrected gated PET images corresponding to physiological phases other than the reference physiological phase from the attenuation corrected gated PET images. For each of the one or more second attenuation corrected gated PET images, the system may transform the second attenuation corrected gated PET image to generate a transformed gated PET image corresponding to the reference physiological phase. Further, the system may generate the target PET image based on the first attenuation corrected gated PET image and the one or more transformed gated PET images.

In some embodiments, the system may further perform the following operations. The system may obtain a second attenuation map of the subject generated based on a computed tomography (CT) scan of the subject. The system may also select a reference attenuation map that has the highest similarity to the second attenuation map from the first attenuation maps corresponding to the plurality of physiological phases. The system may determine the physiological phase corresponding to the reference attenuation map as the reference physiological phase.

In some embodiments, for each of the one or more second attenuation corrected gated PET images, to transform the second attenuation corrected gated PET image to generate a transformed gated PET image corresponding to the reference physiological phase, the system may further perform the following operations. The system may determine a target region of the subject that is affected by the physiological motion of the subject. For each of the one or more second attenuation corrected gated PET images, the system may determine a motion field between a first region of the first attenuation corrected gated PET image corresponding to the target region and a second region of the second attenuation corrected gated PET image corresponding to the target region. Further, the system may transform the second region in the second attenuation corrected gated PET image based on the motion field to generate the transformed gated PET image corresponding to the reference physiological phase.

In some embodiments, the system may further perform the following operations. The system may obtain a second attenuation map of the subject generated based on a computed tomography (CT) scan of the subject. The system may determine a motion field between the second attenuation map and the first attenuation map corresponding to the reference physiological phase. Further, the system may generate a physiological phase-matched PET image corresponding to the CT scan based on the motion field and the target PET image.

In some embodiments, the plurality of gated PET images may be histoimages.

In some embodiments, the plurality of gated PET images may be non-attenuation corrected (NAC) PET images.

According to another aspect of the present disclosure, a method for PET imaging may be provided. The method may be implemented on a computing device having at least one storage device and at least one processor. The method may include obtaining PET data of a subject collected by a PET scan of the subject and a physiological signal relating to a physiological motion of the subject during the PET scan. The method may also include generating, based on the PET data and the physiological signal, a plurality of gated PET images corresponding to a plurality of physiological phases of the subject. The method may also include, for each of the plurality of physiological phases, generating a first attenuation map of the subject corresponding to the physiological phase based on the gated PET image corresponding to the physiological phase. The method may also include, for each of the plurality of physiological phases, generating an attenuation corrected gated PET image corresponding to the physiological phase based on the first attenuation map and a portion of the PET data corresponding to the physiological phase. The method may further include generating a target PET image corresponding to a reference physiological phase among the plurality of physiological phases based on the attenuation corrected gated PET images corresponding to the plurality of physiological phases.

According to yet another aspect of the present disclosure, a system d for PET imaging may be provided. The system may include an obtaining module, a first generation module, a second generation module, a third generation module, and a fourth generation module. The obtaining module may be configured to obtain PET data of a subject collected by a PET scan of the subject and a physiological signal relating to a physiological motion of the subject during the PET scan. The first generation module may be configured to generate a plurality of gated PET images corresponding to a plurality of physiological phases of the subject based on the PET data and the physiological signal. The second generation module may be configured to, for each of the plurality of physiological phases, generate a first attenuation map of the subject corresponding to the physiological phase based on the gated PET image corresponding to the physiological phase. The third generation module may be configured to, for each of the plurality of physiological phases, generate an attenuation corrected gated PET image corresponding to the physiological phase based on the first attenuation map and a portion of the PET data corresponding to the physiological phase. The fourth generation module may be configured to generate a target PET image corresponding to a reference physiological phase among the plurality of physiological phases based on the attenuation corrected gated PET images corresponding to the plurality of physiological phases.

According to yet another aspect of the present disclosure, a non-transitory computer readable medium may be provided. The non-transitory computer readable medium may comprise at least one set of instructions for PET imaging. When executed by one or more processors of a computing device, the at least one set of instructions may cause the computing device to perform a method. The method may include obtaining PET data of a subject collected by a PET scan of the subject and a physiological signal relating to a physiological motion of the subject during the PET scan. The method may also include generating, based on the PET data and the physiological signal, a plurality of gated PET images corresponding to a plurality of physiological phases of the subject. The method may also include, for each of the plurality of physiological phases, generating a first attenuation map of the subject corresponding to the physiological phase based on the gated PET image corresponding to the physiological phase. The method may also include, for each of the plurality of physiological phases, generating an attenuation corrected gated PET image corresponding to the physiological phase based on the first attenuation map and a portion of the PET data corresponding to the physiological phase. The method may further include generating a target PET image corresponding to a reference physiological phase among the plurality of physiological phases based on the attenuation corrected gated PET images corresponding to the plurality of physiological phases.

According to yet another aspect of the present disclosure, a device for PET imaging may be provided. The device may include at least one processor and at least one storage device for storing a set of instructions. When the set of instructions are executed by the at least one processor, the device may perform the methods of the present disclosure.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
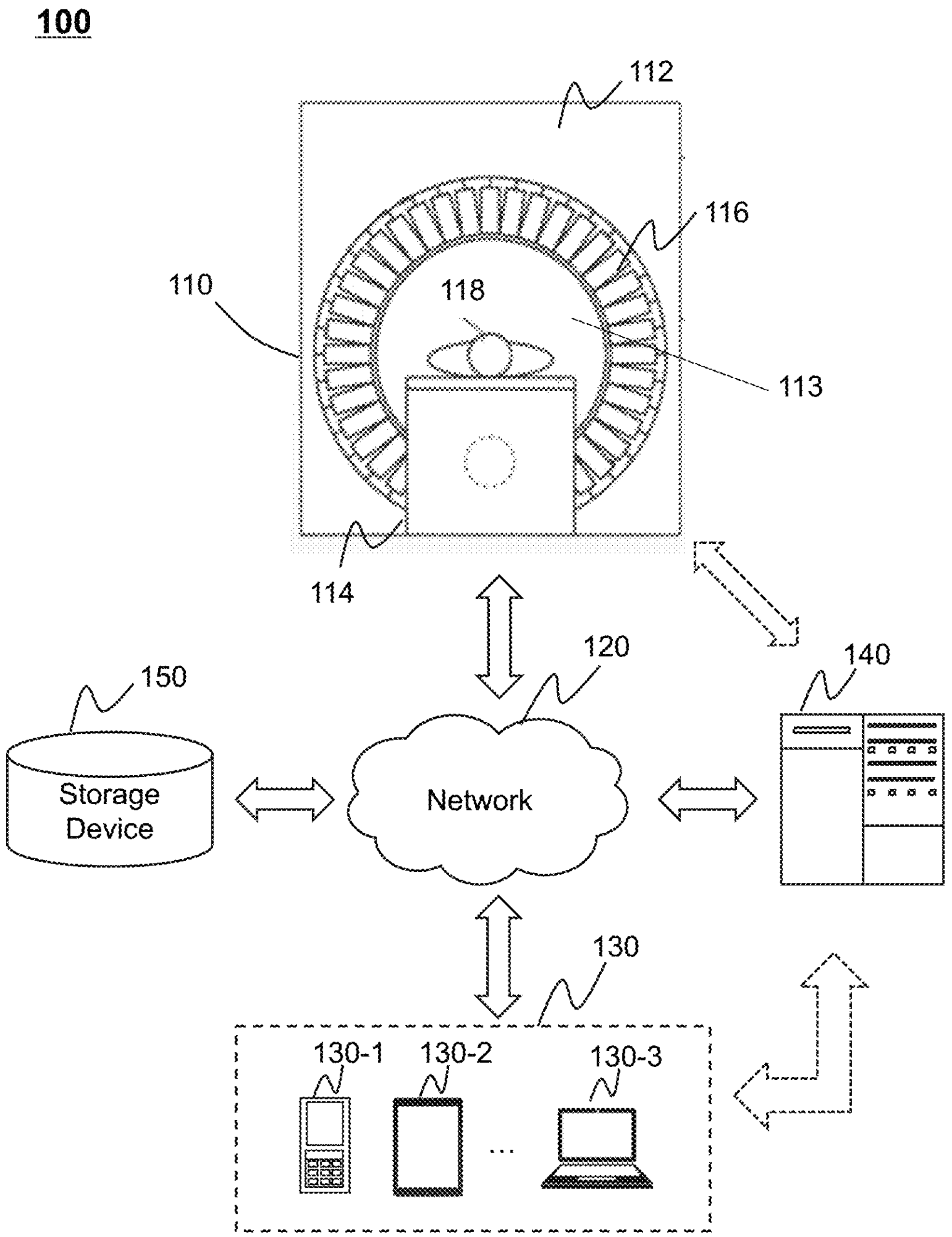
FIG. 1 is a schematic diagram illustrating an exemplary PET system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "pixel" and "voxel" in the present disclosure are used interchangeably to refer to an element of an image. An anatomical structure shown in an image of a subject (e.g., a patient) may correspond to an actual anatomical structure existing in or on the subject's body. The term "object" and "subject" in the present disclosure are used interchangeably to refer to a biological object (e.g., a patient, an animal) or a non-biological object (e.g., a phantom). In some embodiments, the object may include a specific part, organ, and/or tissue of the object. For example, the object may include the head, the bladder, the brain, the neck, the torso, a shoulder, an arm, the thorax, the heart, the stomach, a blood vessel, soft tissue, a knee, a foot, or the like, or any combination thereof, of a patient.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

A PET scan may be used in conjunction with a CT scan to achieve simultaneous acquisition of both structural and functional information of the subject. A CT scan and the PET scan are performed on a same subject to obtain CT data and the PET data. The PET data is gated into multiple sets of gated PET data, and an attenuation map is generated based on the CT data for performing attenuation correction of the gated PET data. Conventional physiological motion correction approaches usually generate attenuation corrected gated PET images by reconstructing the sets of gated PET data based on an attenuation map, further transform the attenuation corrected gated PET images to generate transformed gated PET images corresponding to the same physiological phase, and finally generate a target PET image of the subject by summing the transformed gated PET images. However, a CT scan is quick and the CT data may correspond to the same or substantially the same physiological phase, while the sets of gated PET data may correspond to a plurality of physiological phases, that is, phases of the sets of gated PET data and the attenuation map of the subject generated based on CT scan are usually different, which may obtain attenuation corrected gated PET images with low accuracy, and subsequently cause artifacts in the target PET image, thereby the target PET image having a low accuracy, which in turn may affect an interpretation of the target PET image, or a diagnosis performed based on the target PET image. Moreover, the conventional physiological motion correction approaches focus on how to reduce displacements between the gated PET images by performing physiological motion correction on the gated PET images and do not take into account the mismatch of the phases between the target PET image and the CT image generated based on the CT scan of the subject, which may cause that a fusion image of the target PET image and the CT image has a low accuracy. Therefore, it is desirable to provide systems and methods for physiological motion correction in PET imaging with improved image quality.

As aspect of the present disclosure provides systems and methods for PET imaging. The systems may obtain PET data of a subject collected by a PET scan of the subject and a physiological signal relating to a physiological motion of the subject during the PET scan. The systems may generate a plurality of gated PET images corresponding to a plurality of physiological phases of the subject based on the PET data and the physiological signal. For each of the plurality of physiological phases, the systems may generate a first attenuation map of the subject corresponding to the physiological phase based on the gated PET image corresponding to the physiological phase, and further generate an attenuation corrected gated PET image corresponding to the physiological phase based on the first attenuation map and a portion of the PET data (i.e., a set of gated PET data) corresponding to the physiological phase. Then, the systems may generate a target PET image corresponding to a reference physiological phase among the plurality of physiological phases based on the attenuation corrected gated PET images corresponding to the plurality of physiological phases.

Compared with the conventional physiological motion correction approaches, the methods and systems of the present disclosure may generate attenuation corrected gated PET images with improved attenuation correction effect by using the first attenuation maps that have matched physiological phases with the sets of gated PET data, thereby improving the image quality of the target PET image, that is, improving the imaging quality of the PET imaging.

In additional, according to some embodiments, the systems may further obtain a second attenuation map of the subject generated based on a CT scan of the subject, and determine a motion field between the second attenuation map and the first attenuation map corresponding to the reference physiological phase. Then, the systems may generate a physiological phase-matched PET image corresponding to the CT scan based on the motion field and the target PET image. In this way, the methods and systems of the present disclosure may further improve the imaging quality of the PET imaging by performing a physiological motion correction on the target PET image relative to the CT image.

FIG. 1 is a schematic diagram illustrating an exemplary PET system according to some embodiments of the present disclosure. In some embodiments, as illustrated in FIG. 1, the PET system 100 may include a PET scanner 110, a network 120, a terminal device 130, a processing device 140, and a storage device 150. The components of the PET system 100 may be connected in various manners.

The PET scanner 110 may be configured to acquire scan data relating to an object. For example, the PET scanner 110 may scan the object or a portion thereof that is located within its detection region and generate the scan data relating to the object or the portion thereof.

In some embodiments, the PET scanner 110 may include a gantry 112, a couch 114, and a detector 116. The gantry 112 may support the detector 116. The couch 114 may be used to support an object 118 to be scanned. The detector 116 may include a plurality of detector rings arranged along an axial direction (e.g., Z-axis direction in FIG. 1) of the gantry 112. In some embodiments, a detector ring may include a plurality of detector units arranged along the circumference of the detector ring. In some embodiments, the detector 116 may include a scintillation detector (e.g., a cesium iodide detector), a gas detector, or the like, or any combination thereof.

In some embodiments, before a PET scanning, the object 118 may be injected with a tracer species. The tracer species may refer to a radioactive substance that decays and emits positrons. In some embodiments, the tracer species may be radioactively marked radiopharmaceutical, which is a drug having radioactivity and is administered to the object 118. For example, the tracer species may include fluorine-18 (18F) fluorodeoxyglucose (FDG), etc. During the scanning, pairs of photons (e.g., gamma photons) may result from the annihilation of positrons originating from the tracer species in the object 118. A pair of photons may travel in opposite directions. At least a part of the pairs of photons may be detected and/or registered by the detector units in the detector 116. A coincidence event may be recorded when a pair of photons generated by the positron-electron annihilation are detected within a coincidence time window (e.g., within 6 to 12 nanoseconds). The coincidence event may be assumed to occur along a line connecting a pair of detector units, and the line may be called as a "line of response" (LOR). The detector 116 may obtain counts of coincidence events based on the LORs for detected coincidence events and time points at which the coincidence events occurred.

In some embodiments, the PET scanner 110 may also be a multi-modality scanner, for example, a positron emission tomography-computed tomography (PET-CT) scanner, etc.

The network 120 may facilitate exchange of information and/or data. In some embodiments, one or more components (e.g., the PET scanner 110, the terminal device 130, the processing device 140, the storage device 150) of the PET system 100 may send information and/or data to other component(s) of the PET system 100 via the network 120. For example, the processing device 140 may obtain, via the network 120, scan data relating to the object 118 or a portion thereof from the PET scanner 110. In some embodiments, the network 120 may be any type of wired or wireless network, or a combination thereof.

The terminal device 130 may include a mobile device 130-1, a tablet computer 130-2, a laptop computer 130-3, or the like, or any combination thereof. In some embodiments, the terminal device 130 may remotely operate the PET scanner 110. In some embodiments, the terminal device 130 may operate the PET scanner 110 via a wireless connection. In some embodiments, the terminal device 130 may receive information and/or instructions inputted by a user, and send the received information and/or instructions to the PET scanner 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

The processing device 140 may process data obtained from the PET scanner 110, the terminal device 130, the storage device 150, or other components of the PET system 100. In some embodiments, the processing device 140 (e.g., one or more modules illustrated in FIG. 2) may perform the methods of the present disclosure. For example, any one of processes 300, 400, or 500 may be implemented as a set of instructions (e.g., an application) stored in a storage device (e.g., the storage device 150). The processing device 140 may execute the set of instructions and may accordingly be directed to perform the processes 300, 400, or 500. Merely by way of example, the processing device 140 may obtain scan data (e.g., PET data) of an object (e.g., a human body) from the PET scanner 110 or the storage device 150, and generate a target PET image or a respiratory phase-matched PET image of the object based on the scan data of the object by performing the process 300.

In some embodiments, the processing device 140 may be a single server or a server group. The server group may be centralized or distributed. In some embodiments, the processing device 140 may be local or remote. Merely for illustration, only one processing device 140 is described in the medical system 100. However, it should be noted that the medical system 100 in the present disclosure may also include multiple processing devices. Thus operations and/or method steps that are performed by one processing device 140 as described in the present disclosure may also be jointly or separately performed by the multiple processing devices. For example, if in the present disclosure the processing device 140 of the medical system 100 executes both process A and process B, it should be understood that the process A and the process B may also be performed by two or more different processing devices jointly or separately in the medical system 100 (e.g., a first processing device executes process A and a second processing device executes process B, or the first and second processing devices jointly execute processes A and B).

The storage device 150 may store data, instructions, and/or any other information. In some embodiments, the storage device 150 may store data obtained from the processing device 140, the terminal device 130, and/or the PET scanner 110. For example, the storage device 150 may store scan data collected by the PET scanner 110. As another example, the storage device 150 may store the target PET image of the object. In some embodiments, the storage device 150 may store data and/or instructions that the processing device 140 may execute or use to perform exemplary methods described in the present disclosure.

It should be noted that the above description of the PET system 100 is merely provided for the purposes of illustration, and not intended to limit the scope of the present disclosure. For persons having ordinary skills in the art, multiple variations and modifications may be made under the teachings of the present disclosure. For example, the PET system 100 may include one or more additional components and/or one or more components of the PET system 100 described above may be omitted. Additionally or alternatively, two or more components of the PET system 100 may be integrated into a single component. A component of the PET system 100 may be implemented on two or more sub-components.

Figure 2:
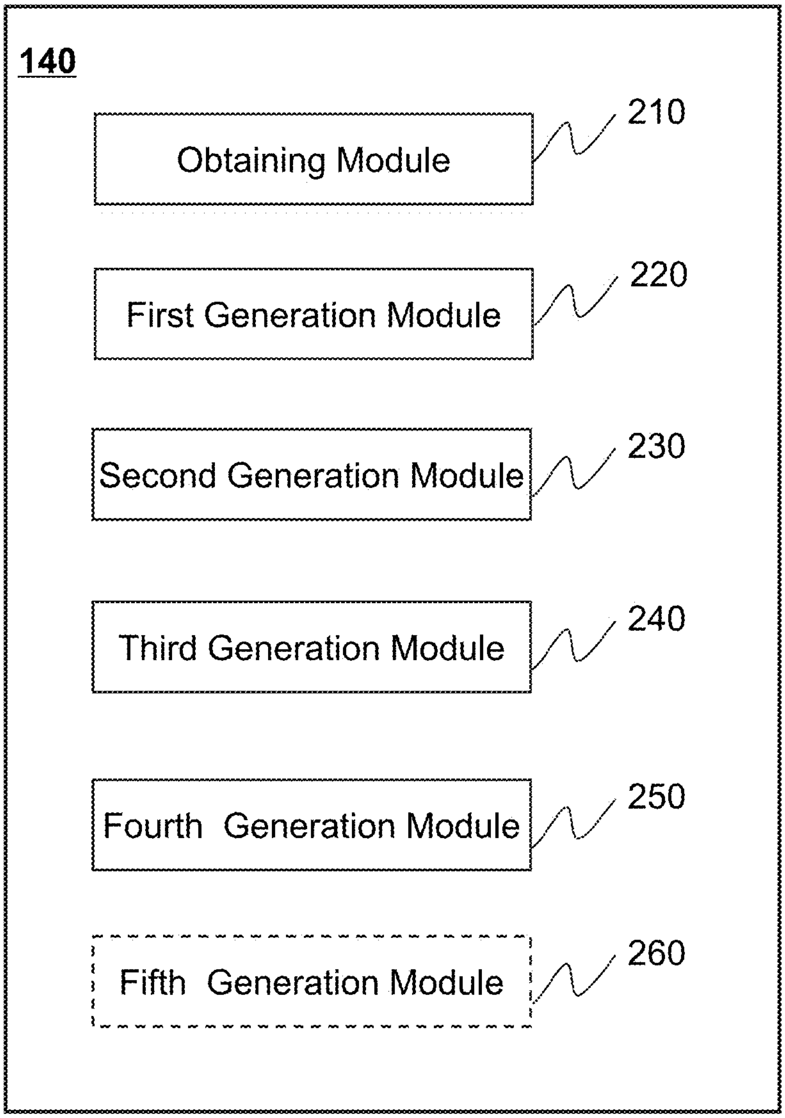
FIG. 2 is a block diagram illustrating exemplary processing device according to some embodiments of the present disclosure.

FIG. 2 is a block diagram illustrating exemplary processing device according to some embodiments of the present disclosure.

As shown in FIG. 2, the processing device 140 may include an obtaining module 210, a first generation module 220, a second generation module 230, a third generation module 240, a fourth generation module 250. In some embodiments. the processing device 140 may further include a fifth generation module 260. As described in FIG. 1, the medical system 100 in the present disclosure may also include multiple processing devices, and the first generation module 220, the second generation module 230, the third generation module 240, the fourth generation module 250, and the fifth generation module 260 may be components of different processing devices.

The obtaining module 210 may be configured to obtain PET data of a subject collected by a PET scan of the subject and a physiological signal relating to a physiological motion of the subject during the PET scan. More descriptions regarding the obtaining of the PET data of the subject may be found elsewhere in the present disclosure. See, e.g., operation 310 in FIG. 3, and relevant descriptions thereof.

The first generation module may be configured to generate a plurality of gated PET images corresponding to a plurality of physiological phases of the subject based on the PET data and the physiological signal. More descriptions regarding the generation of the plurality of gated PET images may be found elsewhere in the present disclosure. See, e.g., operation 320 in FIG. 3, and relevant descriptions thereof.

The second generation module may be configured to, for each of the plurality of physiological phases, generate a first attenuation map of the subject corresponding to the physiological phase based on the gated PET image corresponding to the physiological phase. More descriptions regarding the generation of the first attenuation map of the subject may be found elsewhere in the present disclosure. See, e.g., operation 330 in FIG. 3, and relevant descriptions thereof.

The third generation module may be configured to, for each of the plurality of physiological phases, generate an attenuation corrected gated PET image corresponding to the physiological phase based on the first attenuation map and a portion of the PET data corresponding to the physiological phase. More descriptions regarding the generation of the attenuation corrected gated PET image corresponding to the physiological phase may be found elsewhere in the present disclosure. See, e.g., operation 340 in FIG. 3, and relevant descriptions thereof.

The fourth generation module may be configured to generate a target PET image corresponding to a reference physiological phase among the plurality of physiological phases based on the attenuation corrected gated PET images corresponding to the plurality of physiological phases. More descriptions regarding the generation of the target PET image corresponding to the reference physiological phase may be found elsewhere in the present disclosure. See, e.g., operation 350 in FIG. 3, and relevant descriptions thereof.

The fifth generation module 260 may be configured generate a physiological phase-matched PET image based on the target PET image. The physiological phase-matched PET image may have a matched physiological phase (e.g., the same physiological phase or substantially the same physiological phase) with the CT image. More descriptions regarding the generation of the physiological phase-matched PET image may be found elsewhere in the present disclosure. See, e.g., operation 360 in FIG. 3, and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, any one of the modules may be divided into two or more units. For instance, the obtaining module 210 may be divided into two units configured to acquire different data. In some embodiments, the processing device 140 may include one or more additional modules, such as a storage module (not shown) for storing data.

Figure 3:
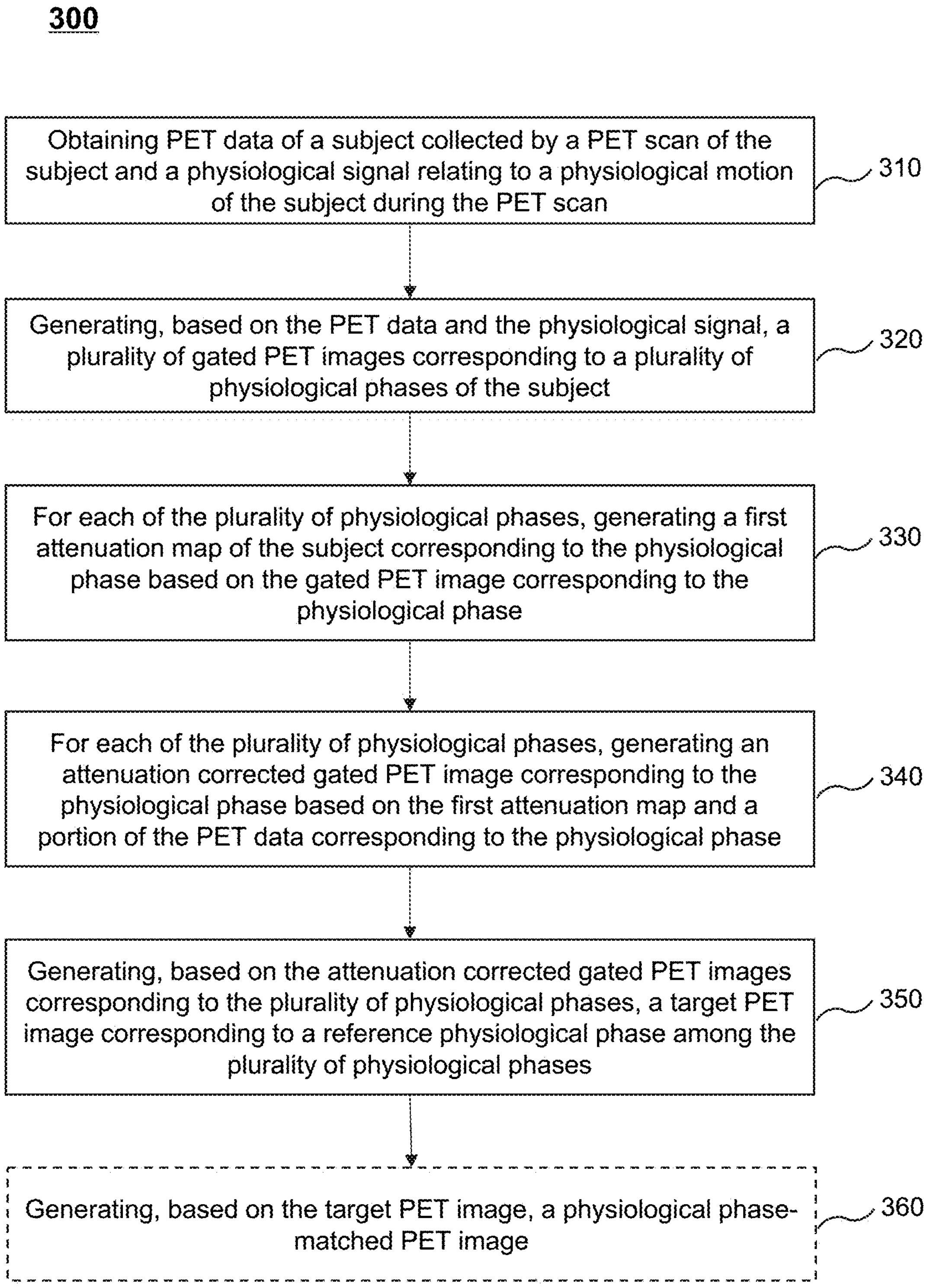
FIG. 3 is a flowchart illustrating an exemplary process for generating a target PET image according to some embodiments of the present disclosure.

FIG. 3 is a flowchart illustrating an exemplary process for generating a target PET image according to some embodiments of the present disclosure.

In 310, the processing device 140 (e.g., the obtaining module 210) may obtain PET data of a subject collected by a PET scan of the subject and a physiological signal relating to a physiological motion of the subject during the PET scan.

In some embodiments, the physiological motion may include a cardiac motion, a respiratory motion, etc. The physiological signal is generated by the physiological motion. Exemplary physiological signals may include a heartbeat signal, a breathing signal, or the like, or any combination thereof.

In some embodiments, the PET data may be collected by scanning a region of interest (ROI) of the subject via the PET scanner 110. The subject may include a patient, an animal, a phantom, or a portion thereof including, for example, an artificial limb, an artificial heart, a tumor, any structure or organ that may be examined using X-ray, or the like, or any combination thereof. The ROI may include any part of the subject. For example, the ROI may include a whole body of the subject. Alternatively, the ROI may be a portion of the subject, such as a brain, a lung, a liver, a kidney, a bone, etc. In some embodiments, the ROI may include at least a portion of a thorax and an abdomen of the subject.

In some embodiments, the PET scan may be performed at one or more couch positions, that is, the PET data may include data collected when the couch is at one or more specific positions. In some embodiments, the processing device 140 may directly obtain the PET data from the PET scanner 110. In some embodiments, the PET data may be previously collected and stored in a storage device (e.g., the storage device 150, or an external source). The processing device 140 may retrieve the PET data directly from the storage device.

In some embodiments, the processing device 140 may generate the physiological signal based on the PET data of the subject.

In some embodiments, the processing device 140 may determine a target region of the subject that is affected by the physiological motion of the subject. For example, the target region may include at least a portion in a thoracic and abdominal region of the subject. Merely by way of example, the target region may correspond to a portion in a thoracic and abdominal region of the subject surrounded by the ribs and the spine of the subject, and the ribs and the spine of the subject may be excluded from the target region. As used herein, the thoracic and abdominal region may refer to the region including the thoracic and abdominal cavity and the muscle skin of the ribs and the spine surrounding the thoracic and abdominal cavity. When the subject breaths during a scan, the internal organs within the thoracic and abdominal region may move (the movement may be referred to as a physiological motion). The portion outside the thoracic and abdominal cavity may undergo no or little physiological motion.

Further, the processing device 140 may determine a time activity curve (TAC) corresponding to the target region based on the PET data. Specifically, the processing device 140 may divide the PET data into multiple sets of PET data each of which is collected in a time period (e.g., 100 milliseconds, 150 milliseconds, etc.) during the PET scan. For each of the multiple sets of PET data, the processing device 140 may reconstruct an initial PET image, and determine an average of pixels of a region of the initial PET image corresponding to the target region of the subject. Further, the processing device 140 may generate the TAC corresponding to the target region based on the time periods and the average of pixels corresponding to the initial PET images. For example, the processing device 140 may determine points in a first coordinate system based on the time periods and the average of pixels corresponding to the initial PET images, wherein the first coordinate system has the time and the average of pixel as two coordinate axises. Then, the processing device 140 may generate a TAC corresponding to the target region by fitting the points in the first coordinate system.

Then, the processing device 140 may generate the physiological signal of the subject based on the TAC. For example, the processing device 140 may generate a frequency curve corresponding to the TAC by converting the TAC from a time-domain signal to a frequency-domain signal. The processing device 140 may perform a filtering operation on the frequency curve to generate a target frequency curve corresponding to the physiological signal. Further, processing device 140 may generate the physiological signal by converting the target frequency curve from the frequency-domain signal to the time-domain signal.

In some embodiments, for each of time points during the PET scan, the processing device 140 may determine a centroid of distribution (COD) of coincidence events in the target region at the time point based on the PET data. Further, the process device 120 may generate the physiological signal of the subject based on the COD corresponding to each of the time points. For example, the processing device 140 may determine points in a second coordinate system based on the time points and the corresponding CODs, wherein the second coordinate system has the time and the COD as two coordinate axises. Then, the processing device 140 may generate a COD curve corresponding to the target region by fitting the points in the second coordinate system.

In some embodiments, the CODs of the time points may be represented by three-dimensional (3D) spatial positions. The processing device 140 may generate three COD curves each of which corresponds to one dimension of the 3D spatial positions. The processing device 140 may select one of the three COD curves as a target COD curve. For example, the processing device 140 may select one COD curve with the greatest signal to noise ratio from the three COD curves as the target COD curve. Then, the process device 120 may generate the physiological signal of the subject based on the target COD curve. For example, the processing device 140 may generate the physiological signal of the subject in a similar manner as how to generate the physiological signal based on the TAC.

In some embodiments, the respiration signal may be acquired from a source other than the PET data. For instance, the respiration signal may be collected via a physiological detection device (e.g., a chest strap, a chest reflector module, a radar device, etc.). The processing device 140 may obtain the physiological signal from the physiological detection device.

In 320, the processing device 140 (e.g., the first generation module 220) may generate, based on the PET data and the physiological signal, a plurality of gated PET images corresponding to a plurality of physiological phases of the subject.

In some embodiments, exemplary physiological phases of the subject may include an intermediate inspiratory phase, an end-inspiratory phase, an intermediate expiratory phase, an end-expiratory phase, or the like, or any combination thereof.

In some embodiments, the physiological signal may be divided into a plurality of parts each of which corresponds to one of the plurality of physiological phases. In some embodiments, the physiological signal may be divided according to an amplitude of the physiological signal. For example, a cycle of the physiological signal may be divided based on the amplitude of the physiological signal. The amplitude of the physiological signal is evenly segmented into n parts (e.g., from the maximum amplitude to the minimum amplitude), thereby generating n portions of the physiological signal corresponding to n physiological phases. In some embodiments, the physiological signal may be divided into N parts based on the time of the physiological signal, and the N parts may correspond to N physiological phases. For example, if a cycle of the physiological signal lasts 5 seconds, a cycle of the physiological signal may be divided according to a unit interval (e.g., 0.5 seconds, or 1 second), and this cycle of the physiological signal may be divided into N physiological phases (e.g., 5/0.5 physiological phases, or 5/1 physiological phases). In some embodiments, the physiological signal may be divided according to a count of coincidence events. For example, a cycle of the physiological signal may be divided into the plurality of physiological phases according to a same count of coincidence events, that is, substantially the same amount of coincidence events are detected in each physiological phase. The plurality of physiological phases may correspond to the same count of coincidence events.

Further, the processing device 140 may gate the PET data into a plurality of groups of gated PET data based on the plurality of physiological phases of the respiration signal. Each group of gated PET data may correspond to one of the plurality of physiological phases. For example, the physiological signal may include N physiological phases, and the processing device 140 may gate the PET data into N groups of gated PET data each of which corresponds to one of the N physiological phases. A group of gated PET data corresponding to a specific physiological phase is collected when the subject is in the specific physiological phase.

In some embodiments, the processing device 140 may reconstruct a gated PET image for each physiological phase based on the corresponding group of gated PET data using a reconstruction algorithm. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof. Since the reconstruction in operation 320 is performed without any attenuation maps, the reconstructed images generated in operation 320 may be regarded as gated PET images without attenuation correction.

In some embodiments, the PET data may be in forms of listmode, sinogram, etc. The gated PET images may be in forms of non-attenuation corrected (NAC) PET image, histoimage.

In 330, for each of the plurality of physiological phases, the processing device 140 (e.g., the second generation module 230) may generate a first attenuation map of the subject corresponding to the physiological phase based on the gated PET image corresponding to the physiological phase.

In a PET scan, attenuation to various extents may occur when γ-rays pass through different tissues of a subject because the attenuation degrees of different tissues to γ-rays are different, causing distortion of a PET image and/or PET scan data. In PET reconstruction, attenuation correction needs to be performed. An attenuation map of a subject may indicate tissue attenuation coefficients corresponding to different portions (e.g., different organs, different tissues) of the subject.

Conventionally, the same attenuation map is used for reconstructing attenuation corrected gated PET images corresponding to different physiological phases, and the attenuation correction effect on the attenuation corrected gated PET images is not desired. In the present disclosure, different first attenuation maps corresponding to different physiological phases are generated for generating the attenuation corrected gated PET images, so as to improve the attenuation correction effect. In addition, it should be noted that the first attenuation maps disclosed herein are generated based on the gated PET images instead of CT data, and the first attenuation maps may be regarded as predicted or simulated attenuation maps.

In some embodiments, for each of the plurality of physiological phases, the processing device 140 may generate the first attenuation map of the subject corresponding to the physiological phase by processing the gated PET image corresponding to the physiological phase using an attenuation map generation model. The attenuation map generation model may be a trained machine learning model for generating an attenuation map. Merely by way of example, the gated PET image corresponding to a physiological phase may be input into the attenuation map generation model, the attenuation map generation model may output the first attenuation map of the subject corresponding to the physiological phase. The attenuation map generation model may be a deep learning model, such as a deep neural network (DNN) model, a convolutional neural network (CNN) model, a recurrent neural network (RNN) model, a feature pyramid network (FPN) model, a generative adversarial network (GAN) model, a Transformer model, a diffusion model, etc. Exemplary CNN models may include a V-Net model, a U-Net model, a Link-Net model, or the like, or any combination thereof. According to some embodiments, the first attenuation maps of the subject may be generated using the attenuation map generation model, which may greatly reduce the radiation to the subject. Moreover, since the attenuation map generation model may learn the optimal mechanism for generating attenuation maps based on a large amount of data, the first attenuation maps generated using the attenuation map generation model may be relatively accurate.

In some embodiments, the processing device 140 may obtain the attenuation map generation model from one or more components of the PET system 100 (e.g., the storage device 150, the terminals(s) 130) or an external source via a network (e.g., the network 120). For example, the attenuation map generation model may be previously trained by a computing device (e.g., the processing device 140), and stored in a storage device (e.g., the storage device 150) of the PET system 100. The processing device 140 may access the storage device and retrieve the attenuation map generation model. In some embodiments, the attenuation map generation model may be generated according to process 400.

In 340, for each of the plurality of physiological phases, the processing device 140 (e.g., the third generation module 240) may generate an attenuation corrected gated PET image corresponding to the physiological phase based on the first attenuation map and a portion of the PET data corresponding to the physiological phase.

In some embodiments, for each of the plurality of physiological phases, the processing device 140 may reconstruct the attenuation corrected gated PET image corresponding to the physiological phase based on the first attenuation map and the group of gated PET data corresponding to the physiological phase using a reconstruction algorithm described in elsewhere of the present disclosure. Since the reconstruction in operation 340 is performed with the first attenuation maps, the reconstructed images generated in operation 340 may be regarded as attenuation corrected gated PET images.

In 350, the processing device 140 (e.g., the fourth generation module 250) may generate, based on the attenuation corrected gated PET images corresponding to the plurality of physiological phases, a target PET image corresponding to a reference physiological phase among the plurality of physiological phases.

In some embodiments, the processing device 140 or a user may select one physiological phase from the plurality of physiological phases as the reference physiological phase. For example, the processing device 140 randomly select one physiological phase from the plurality of physiological phases as the reference physiological phase. As another example, the user may select the end-expiratory phase as the reference physiological phase. For brevity, the first attenuation map corresponding to the reference physiological phase is referred to as a reference attenuation map.

In some embodiments, the processing device 140 may obtain a second attenuation map of the subject based on a computed tomography (CT) scan of the subject. The CT scan may be performed before or after the PET scan. The fields of view (FOVs) of the CT scan and the PET scan may at least cover the same ROI of the subject. For example, if the ROI of the subject is a chest of the subject, the CT scan of the chest of the subject is first performed, the PET scan of the chest of the subject may be performed when the subject keeps essentially the same patient position. In some embodiments, the processing device 140 may obtain the CT data collected by the CT scan of the subject from the PET system 100 (e.g., a PET-CT scanner) and generate the second attenuation map of the subject generated based on the CT data.

Further, the processing device 140 may determine the reference physiological phase based on a similarity between the second attenuation map and each of the first attenuation map. For example, the processing device 140 may select a reference attenuation map that has the highest similarity to the second attenuation map from the first attenuation maps, and determine the physiological phase corresponding to the reference attenuation map as the reference physiological phase.

The similarity between the second attenuation map and a first attenuation map may be represented by such as mutual information (MI), normalized mutual information (NMI), a mean squared error (MSE), a structural similarity (SSIM), etc., between the two maps. In some embodiments, the processing device 140 may determine the similarities between the second attenuation map and the first attenuation maps using a similarity algorithm. Exemplary similarity algorithms may include an algorithm based on histogram, an algorithm based on Euclidean distance, an algorithm based on Pearson correlation coefficient, an algorithm based on cosine similarity, a hash algorithm, or the like. In this way, the reference physiological phase may have a smallest phase difference from a physiological phase of the CT scan.

In some embodiments, the processing device 140 may determine a first region in a first attenuation map corresponding to the target region of the subject and a second region in the second attenuation map corresponding to the target region of the subject. The processing device 140 may determine a similarity between the first region and the second region, and designate the similarity between the first region and the second region as the similarity between the first attenuation map and the second attenuation map. In this way, the efficiency of the determination of the reference physiological phase may be improved by reducing data processing amount.

In some embodiments, the processing device 140 may determine a first attenuation corrected gated PET image corresponding to the reference physiological phase and one or more second attenuation corrected gated PET images corresponding to physiological phases other than the reference physiological phase from the attenuation corrected gated PET images. Further, for each of the one or more second attenuation corrected gated PET images, the processing device 140 may transform the second attenuation corrected gated PET image to generate a transformed gated PET image corresponding to the reference physiological phase. Then, the processing device 140 may generate the target PET image based on the first attenuation corrected gated PET image and the one or more transformed gated PET images. More descriptions regarding the generation of the target PET image based on the first attenuation corrected gated PET image and the one or more transformed gated PET images may be found elsewhere in the present disclosure (e.g., FIG. 5 and the descriptions thereof).

In some embodiments, the processing device 140 may designate the target PET image as a final PET image of the subject for clinical examination or disease diagnosis, etc.

In some embodiments, the processing device 120 may generate a fusion image including both functional information and anatomical information of the subject by directly combining the target PET image and a CT image generated based on the CT data.

In some embodiments, the processing device 140 may further perform a physiological motion correction on the target PET image relative to the CT image via operation 360 to obtain the fusion image of the subject.

In 360, the processing device 140 (e.g., the fifth generation module 260) may generate, based on the target PET image, a physiological phase-matched PET image.

The physiological phase-matched PET image may have a matched physiological phase (e.g., the same physiological phase or substantially the same physiological phase) with the CT image.

In some embodiments, the processing device 140 may determine a motion field between the second attenuation map and the first attenuation map corresponding to the reference physiological phase (i.e., the reference attenuation map). In some embodiments, the processing device 140 may determine the motion field between the second attenuation map and the reference attenuation map in a similar manner as how the motion field between the second attenuation corrected gated PET image and the first attenuation corrected gated PET image is determined described in operation 520, and the descriptions of which are not repeated here.

Then, the processing device 140 may generate the physiological phase-matched PET image based on the motion field and the target PET image. For example, the processing device 140 may transform (or warp) the target PET image based on the motion field between the second attenuation map and the reference attenuation map to generate the physiological phase-matched PET image. In some embodiments, the processing device 140 may transform the target PET image to generate the physiological phase-matched PET image in a similar manner as how the second attenuation corrected gated PET image is transformed to generate the transformed gated PET image described in operation 520, and the descriptions of which are not repeated here.

The processing device 140 may combine the physiological phase-matched PET image and the CT image into the final PET image of the subject.

As described in elsewhere in the present disclosure, conventional physiological motion correction approaches usually perform attenuation corrections on gated PET images of a subject using an attenuation map of the subject generated based on a CT scan of the subject, which obtain the target PET image with a low accuracy. Compared with the conventional physiological motion correction approaches, according to some embodiments of the present disclosure, the processing device 140 may generate attenuation corrected gated PET images with improved attenuation correction effect by using the first attenuation maps of the subject that have matched physiological phases with the sets of gated PET data, thereby improving the image quality of the target PET image. Moreover, in some embodiments, the processing device 140 may determine the reference physiological phase having a smallest phase difference from the physiological phase of the CT scan based on similarities between the second attenuation map and the first attenuation maps, which can improve the accuracy of the fusion image of the subject obtained by combining the target PET image and the CT image, thereby improving the imaging quality of the PET imaging.

In additional, according to some embodiments, the processing device 140 may generate the physiological phase-matched PET image corresponding to the CT scan by performing a physiological motion correction on the target PET image relative to the CT image, which may can further improve the accuracy of the fusion image of the subject, thereby further improving the imaging quality of the PET imaging.

It should be noted that the above description regarding the process 300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 300 may be accomplished with one or more additional operations not described and/or without one or more of the operations discussed above. For example, the processing device 140 may send the attenuation corrected gated PET images, the target PET image, the physiological phase-matched PET image to a terminal device (e.g., the terminal device 130) for display.

Figure 4:
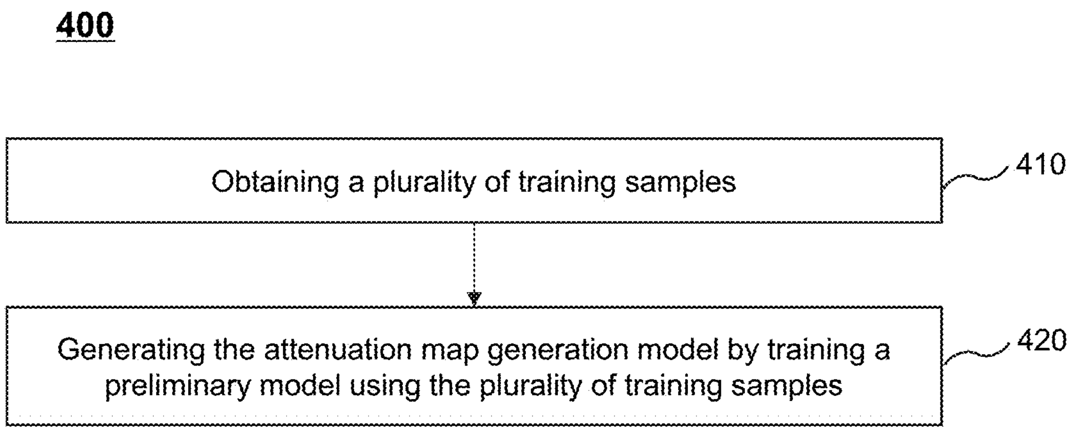
FIG. 4 is a flowchart illustrating an exemplary process for generating an attenuation map generation model according to some embodiments of the present disclosure.

FIG. 4 is a flowchart illustrating an exemplary process for generating an attenuation map generation model according to some embodiments of the present disclosure.

In 410, the processing device 140 (e.g., the second generation module 230) may obtain a plurality of training samples.

In some embodiments, each training sample may include a sample gated PET image and a ground truth attenuation map of a sample subject. The sample gated PET image and the ground truth attenuation map corresponding to the same physiological phase of the sample subject.

In some embodiments, the processing device 140 may generate a training sample based on sample PET data and sample CT data collected by a sample PET scan and a sample CT scan of the sample subject. For example, the processing device 140 may determine a sample reference physiological phase of the sample CT scan based on the sample CT data. Further, the processing device 140 or a user may determine a group of sample gated PET data corresponding to the sample reference physiological phase. The processing device 140 may generate the sample gated PET image based on the group of sample gated PET data. As another example, the processing device 140 may generate multiple initial sample gated PET images based on the sample PET data and a sample CT image based on the sample CT data. Further, the processing device 140 may determine an initial sample gated PET image with the same or substantially the same physiological phase as the sample CT image from the multiple initial sample gated PET images, and designate the initial sample gated PET image as the sample gated PET image. The processing device 140 may generate a sample attenuation map of the sample subject based on the sample CT data, and designate the sample attenuation map of the sample subject as the ground truth attenuation map of the sample subject.

In some embodiments, the plurality of training samples may be previously collected and stored in a storage device (e.g., the storage device 150, or an external source). The processing device 140 may retrieve the plurality of training samples directly from the storage device.

In 420, the processing device 140 (e.g., the second generation module 230) may generate the attenuation map generation model by training a preliminary model using the plurality of training samples.

The preliminary model refers to a model to be trained. The preliminary model may be of any type of model (e.g., a machine learning model) as described elsewhere in this disclosure (e.g., FIG. 3 and the relevant descriptions). The preliminary model may include a plurality of model parameters. Before training, the model parameters of the preliminary model may have their respective initial values.

In the training of the preliminary model, the values of the model parameters may be iteratively updated until a termination condition is satisfied. Merely by way of example, in the current iteration, the processing device 140 may obtain a predicted attenuation map of the sample subject of each training sample by inputting the sample gated PET image of the training sample into the preliminary model of the current iteration. The value of a loss function may be determined to measure the difference between the predicted attenuation maps and the ground truth attenuation maps of the training samples. If the value of the loss function is smaller than a threshold, the termination condition may be satisfied, and the preliminary model may be designated as the attenuation map generation model. Otherwise, the model parameters of the preliminary model may be updated based on the value of the loss function until the termination condition is satisfied.

Other exemplary termination conditions may include that a difference between the values of the loss function obtained in a previous iteration and the current iteration (or among the values of the loss function within a certain number or count of successive iterations) is less than a certain threshold, a maximum number (or count) of iterations has been performed, or the like, or any combination thereof.

In some embodiments, the attenuation map generation model may be generated by a computing device other than the processing device 140, such as a computing device of a vendor of the attenuation map generation model.

Figure 5:
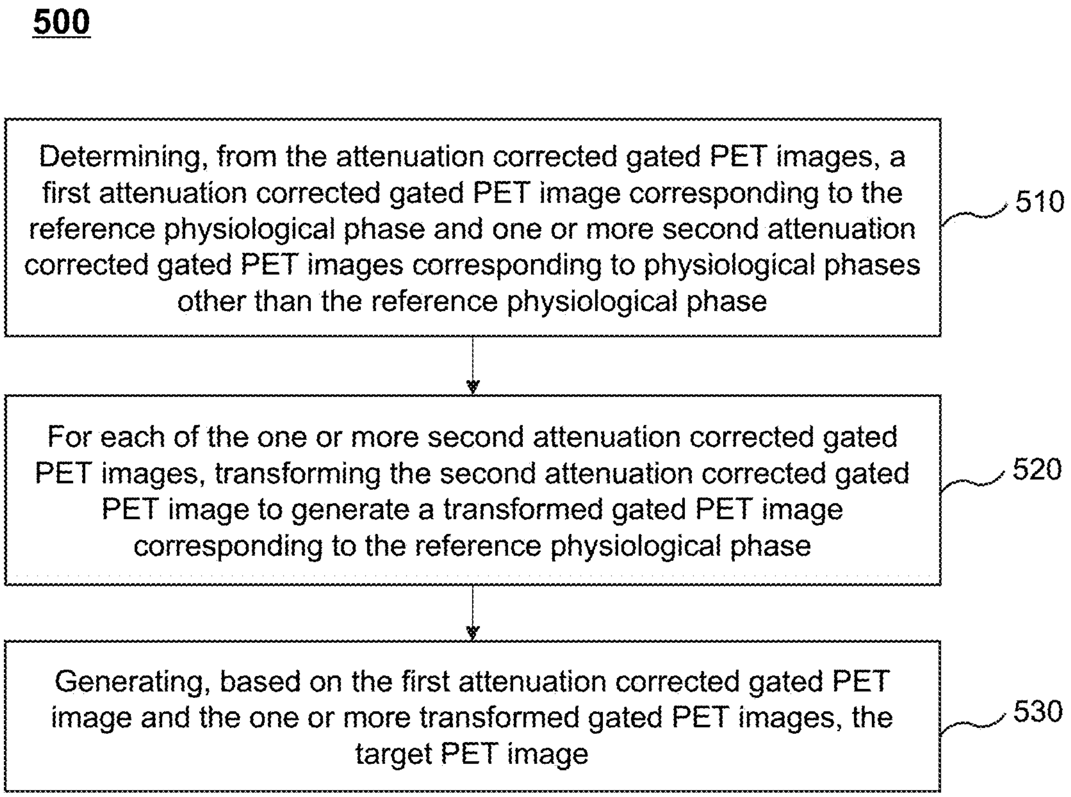
FIG. 5 is a flowchart illustrating an exemplary process for generating a target PET image by performing physiological motion correction according to some embodiments of the present disclosure.

FIG. 5 is a flowchart illustrating an exemplary process for generating a target PET image by performing a physiological motion correction according to some embodiments of the present disclosure.

In 510, the processing device 140 (e.g., the fourth generation module 250) may determine, from the attenuation corrected gated PET images, a first attenuation corrected gated PET image corresponding to the reference physiological phase and one or more second attenuation corrected gated PET images corresponding to physiological phases other than the reference physiological phase.

In 520, for each of the one or more second attenuation corrected gated PET images, the processing device 140 (e.g., the fourth generation module 250) may transform the second attenuation corrected gated PET image to generate a transformed gated PET image corresponding to the reference physiological phase.

In some embodiments, for a second attenuation corrected gated PET image, the processing device 140 may determine a motion field between the second attenuation corrected gated PET image and the first attenuation corrected gated PET image by registering the second attenuation corrected gated PET image and the first attenuation corrected gated PET image. For example, the processing device 140 may register the second attenuation corrected gated PET image with the first attenuation corrected gated PET image based on a registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow algorithm, a B-spline registration algorithm, or the like, or any combination thereof. In some embodiments, the registration may be performed based on rigid transformation, an affine transformation, a projection transformation, a nonlinear transformation, an optical-flow-based registration, a similarity measurement, or the like, or any combination thereof. The motion field may include a plurality of motion vectors corresponding to a plurality of physical points of the subject. A motion vector of a physical point may be used to describe the motion between a point corresponding to the physical point in the second attenuation corrected gated PET image and a point corresponding to the physical point in the first attenuation corrected gated PET image (i.e., the motion of the physical point between a physiological phase corresponding to the second attenuation corrected gated PET image and the reference physiological phase).

Further, the processing device 140 may transform the second attenuation corrected gated PET image based on the motion field to generate the transformed gated PET image corresponding to the reference physiological phase. For example, the processing device 140 may transform locations of the voxels in the second attenuation corrected gated PET image according to the motion field to generate the transformed gated PET image corresponding to the reference physiological phase.

In some embodiments, for each of the one or more second attenuation corrected gated PET images, the processing device 140 may determine a motion field between a first region of the first attenuation corrected gated PET image corresponding to the target region and a second region of the second attenuation corrected gated PET image corresponding to the target region. Further, the processing device 140 may transform the second region in the second attenuation corrected gated PET image based on the motion field between the first region and the second region to generate the transformed gated PET image corresponding to the reference physiological phase. Specifically, the processing device 140 may transform locations of the voxels in the second region according to the motion field between the first region and the second region, and voxels outside the second region in the second attenuation corrected gated PET image may not be transformed. In this way, the efficiency of the generation of the transformed gated PET images may be improved via reducing the data process, and the accuracy of the generation of the transformed gated PET images may be improved by performing the physiological motion correction only on the second region corresponding to the target region, avoiding false corrections on other areas that are not affected by the physiological motion of the subject.

In 530, the processing device 140 (e.g., the fourth generation module 250) may generate, based on the first attenuation corrected gated PET image and the one or more transformed gated PET images, the target PET image.

In some embodiments, the processing device 140 may combine the first attenuation corrected gated PET image and the one or more transformed gated PET images into the target PET image.

Figure 6:
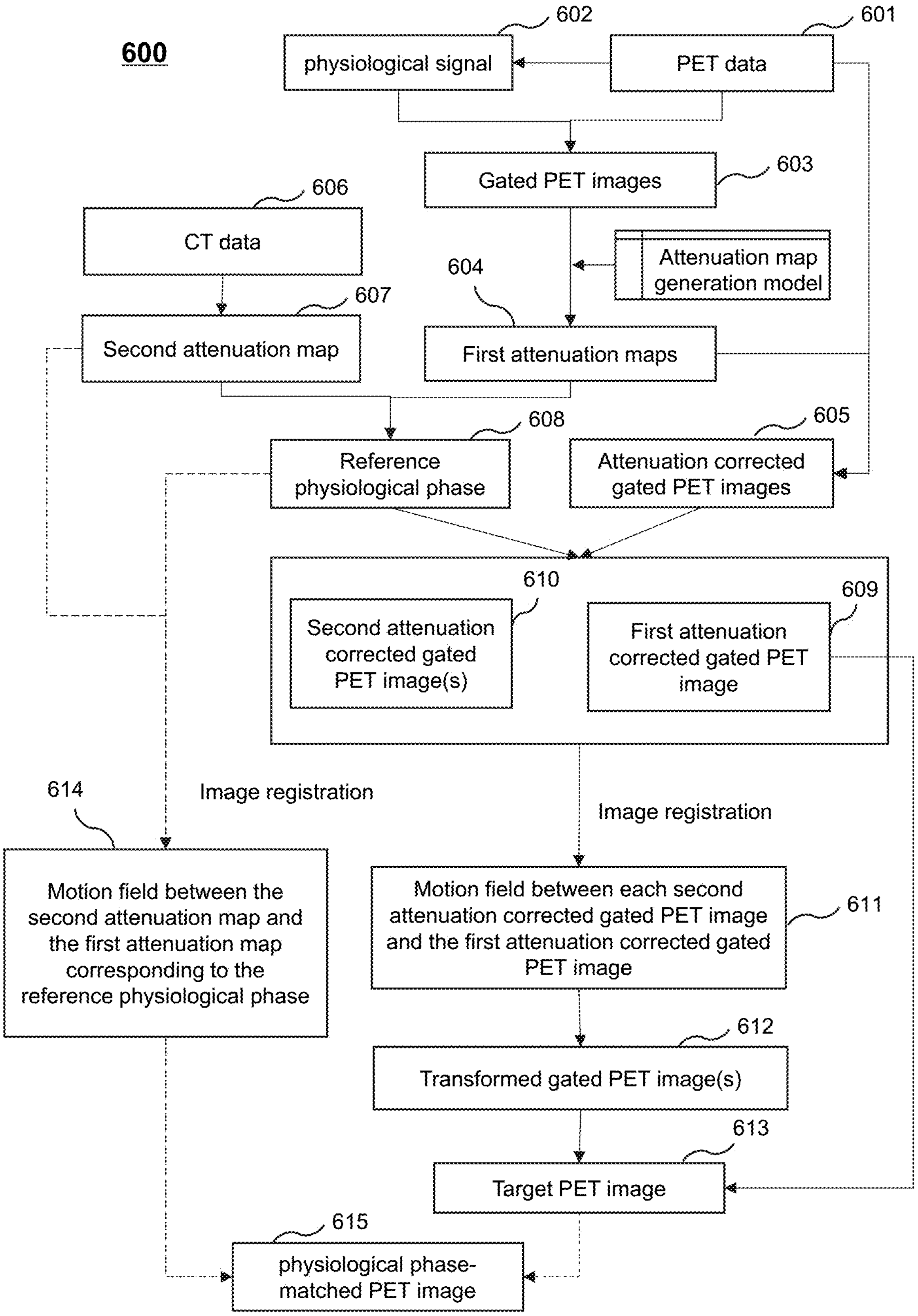
FIG. 6 is a schematic diagram illustrating an exemplary process of PET imaging according to some embodiments of the present disclosure.

FIG. 6 is a schematic diagram illustrating an exemplary process of PET imaging according to some embodiments of the present disclosure. As shown in FIG. 6, PET data 601 and a physiological signal 602 may be obtained. In some embodiments, the physiological signal 602 may be generated based on the PET data 601 as described in operation 310. A plurality of gated PET images 603 may be generated based on the PET data 601 and the physiological signal 602. Further, a plurality of first attenuation maps 604 may be generated based on the plurality of gated PET images 603 using an attenuation map generation model, and a plurality of attenuation corrected gated PET images 605 may be generated based on the plurality of first attenuation maps 604 and the PET data 601.

A reference physiological phase 608 may be determined. In some embodiments, a second attenuation map 607 may be generated based CT data 606, and the reference physiological phase 608 may be determined based on the second attenuation map 607 and the plurality of first attenuation maps 604. Then, a first attenuation corrected gated PET image 609 corresponding to the reference physiological phase and one or more second attenuation corrected gated PET images 610 may be determined from the plurality of attenuation corrected gated PET images 605. A motion field 611 between the first attenuation corrected gated PET image 609 and each second attenuation corrected gated PET image 610 may be determined by performing an image registration between the first attenuation corrected gated PET image 609 and the second attenuation corrected gated PET image 610. Further, one or more transformed gated PET images 612 may be generated by transforming the one or more second attenuation corrected gated PET images 610 based on the motion fields 611. A target PET image 613 may be generated by combining the one or more transformed gated PET images 612 and the first attenuation corrected gated PET image 609.

In some embodiments, a motion field 614 between the second attenuation map and the first attenuation map corresponding to the reference physiological phase 608 (i.e., the reference attenuation map) may be determined by performing an image registration. Finally, the physiological phase-matched PET image 615 may be generated by transforming the target PET image 613 based on the motion field 614.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof. For example, the operations of the illustrated processes 300, 400, and 500 are intended to be illustrative. In some embodiments, the processes 300, 400, and 500 may be accomplished with one or more additional operations not described, and/or without one or more of the operations discussed. Additionally, the order in which the operations of the processes 300, 400, and 500 and regarding descriptions are not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (Saas).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques.

Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A system for positron emission tomography (PET) imaging, comprising:

at least one storage device including a set of instructions; and at least one processor in communication with the at least one storage device, wherein when executing the set of instructions, the at least one processor is configured to direct the system to perform operations including:

obtaining PET data of a subject collected by a PET scan of the subject and a physiological signal relating to a physiological motion of the subject during the PET scan;

generating, based on the PET data and the physiological signal, a plurality of gated PET images corresponding to a plurality of physiological phases of the subject;

for each of the plurality of physiological phases, generating a first attenuation map of the subject corresponding to the physiological phase based on the gated PET image corresponding to the physiological phase;

for each of the plurality of physiological phases, generating an attenuation corrected gated PET image corresponding to the physiological phase based on the first attenuation map and a portion of the PET data corresponding to the physiological phase;

generating, based on the attenuation corrected gated PET images corresponding to the plurality of physiological phases, a target PET image corresponding to a reference physiological phase among the plurality of physiological phases;

obtaining a second attenuation map of the subject generated based on a computed tomography (CT) scan of the subject:

determining a motion field between the second attenuation map and the first attenuation map corresponding to the reference physiological phase; and generating, based on the motion field and the target PET image, a physiological phase-matched PET image corresponding to the CT scan.

2. The system of claim 1, wherein the obtaining a physiological signal relating to a physiological motion of the subject during the PET scan includes:

determining a target region of the subject that is affected by the physiological motion of the subject;

determining, based on the PET data, a time activity curve (TAC) corresponding to the target region; and generating, based on the TAC, the physiological signal of the subject.

3. The system of claim 1, wherein the obtaining a physiological signal relating to a physiological motion of the subject during the PET scan includes:

determining a target region that is affected by the physiological motion of the subject;

for each of time points during the PET scan, determining a centroid of distribution (COD) of coincidence events in the target region at the time point based on the PET data;

generating, based on the COD corresponding to each of the time points, the physiological signal of the subject.

4. The system of claim 3, wherein the generating, based on the COD corresponding to each of the time points, the physiological signal of the subject includes:

representing the CODs of the time points by three-dimensional (3D) spatial positions;

generating three COD curves, each of which corresponds to one dimension of the 3D spatial positions;

selecting one of the three COD curves with the greatest signal-to-noise ratio among the three COD curves as a target COD curve; and generating the physiological signal of the subject based on the target COD curve.

5. The system of claim 1, wherein the for each of the plurality of physiological phases, generating a first attenuation map of the subject corresponding to the physiological phase based on the gated PET image corresponding to the physiological phase includes:

for each of the plurality of physiological phases, generating the first attenuation map of the subject corresponding to the physiological phase by processing the gated PET image corresponding to the physiological phase using an attenuation map generation model, the attenuation map generation model being a trained machine learning model.

6. The system of claim 5, wherein the attenuation map generation model is generated according to a model training process including:

obtaining a plurality of training samples each of which includes a sample gated PET image and a ground truth attenuation map of a sample subject, the sample gated PET image and the ground truth attenuation map corresponding to the same physiological phase of the sample subject; and generating the attenuation map generation model by training a preliminary model using the plurality of training samples.

7. The system of claim 1, wherein the generating, based on the attenuation corrected gated PET images corresponding to the plurality of physiological phases, a target PET image corresponding to a reference physiological phase among the plurality of physiological phases includes:

determining, from the attenuation corrected gated PET images, a first attenuation corrected gated PET image corresponding to the reference physiological phase and one or more second attenuation corrected gated PET images corresponding to physiological phases other than the reference physiological phase;

for each of the one or more second attenuation corrected gated PET images, transforming the second attenuation corrected gated PET image to generate a transformed gated PET image corresponding to the reference physiological phase; and generating, based on the first attenuation corrected gated PET image and the one or more transformed gated PET images, the target PET image.

8. The system of claim 7, wherein the operations further include:

selecting, from the first attenuation maps corresponding to the plurality of physiological phases, a reference attenuation map that has the highest similarity to the second attenuation map;

determining the physiological phase corresponding to the reference attenuation map as the reference physiological phase.

9. The system of claim 8, wherein the similarity between the second attenuation map and the first attenuation map is determined by:

determining a first region in the first attenuation map corresponding to a target region of the subject that is affected by the physiological motion;

determining a second region in the second attenuation map corresponding to the target region;

determining a similarity between the first region and the second region; and designating the similarity between the first region and the second region as the similarity between the first attenuation map and the second attenuation map.

10. The system of claim 9, wherein the determining a target region of the subject that is affected by the physiological motion of the subject includes:

determining a portion in a thoracic and abdominal region of the subject surrounded by ribs and a spine of the subject as the target region, wherein the ribs and the spine of the subject are excluded from the target region.

11. The system of claim 7, wherein the for each of the one or more second attenuation corrected gated PET images, transforming the second attenuation corrected gated PET image to generate a transformed gated PET image corresponding to the reference physiological phase includes:

determining a target region of the subject that is affected by the physiological motion of the subject;

for each of the one or more second attenuation corrected gated PET images, determining a motion field between a first region of the first attenuation corrected gated PET image corresponding to the target region and a second region of the second attenuation corrected gated PET image corresponding to the target region; and transforming the second region in the second attenuation corrected gated PET image based on the motion field to generate the transformed gated PET image corresponding to the reference physiological phase.

12. The system of claim 1, wherein the plurality of gated PET images are histoimages.

13. The system of claim 1, wherein the plurality of gated PET images are non-attenuation corrected (NAC) PET images.

14. A non-transitory computer readable medium, comprising at least one set of instructions for positron emission tomography (PET) imaging, wherein when executed by one or more processors of a computing device, the at least one set of instructions causes the computing device to perform a method, the method comprising:

obtaining PET data of a subject collected by a PET scan of the subject and a physiological signal relating to a physiological motion of the subject during the PET scan;

generating, based on the PET data and the physiological signal, a plurality of gated PET images corresponding to a plurality of physiological phases of the subject;

for each of the plurality of physiological phases, generating a first attenuation map of the subject corresponding to the physiological phase based on the gated PET image corresponding to the physiological phase;

for each of the plurality of physiological phases, generating an attenuation corrected gated PET image corresponding to the physiological phase based on the first attenuation map and a portion of the PET data corresponding to the physiological phase;

generating, based on the attenuation corrected gated PET images corresponding to the plurality of physiological phases, a target PET image corresponding to a reference physiological phase among the plurality of physiological phases;

obtaining a second attenuation map of the subject generated based on a computed tomography (CT) scan of the subject;

determining a motion field between the second attenuation map and the first attenuation map corresponding to the reference physiological phase; and generating, based on the motion field and the target PET image, a physiological phase-matched PET image corresponding to the CT scan.

15. A method for positron emission tomography (PET) imaging being implemented on a computing device having at least one storage device and at least one processor, the method comprising:

obtaining PET data of a subject collected by a PET scan of the subject and a physiological signal relating to a physiological motion of the subject during the PET scan;

generating, based on the PET data and the physiological signal, a plurality of gated PET images corresponding to a plurality of physiological phases of the subject;

for each of the plurality of physiological phases, generating a first attenuation map of the subject corresponding to the physiological phase based on the gated PET image corresponding to the physiological phase;

for each of the plurality of physiological phases, generating an attenuation corrected gated PET image corresponding to the physiological phase based on the first attenuation map and a portion of the PET data corresponding to the physiological phase;

generating, based on the attenuation corrected gated PET images corresponding to the plurality of physiological phases, a target PET image corresponding to a reference physiological phase among the plurality of physiological phases;

obtaining a second attenuation map of the subject generated based on a computed tomography (CT) scan of the subject;

determining a motion field between the second attenuation map and the first attenuation map corresponding to the reference physiological phase; and generating, based on the motion field and the target PET image, a physiological phase-matched PET image corresponding to the CT scan.

16. The method of claim 15, wherein the obtaining a physiological signal relating to a physiological motion of the subject during the PET scan includes:

determining a target region of the subject that is affected by the physiological motion of the subject;

determining, based on the PET data, a time activity curve (TAC) corresponding to the target region; and generating, based on the TAC, the physiological signal of the subject.

17. The method of claim 15, wherein the obtaining a physiological signal relating to a physiological motion of the subject during the PET scan includes:

determining a target region that is affected by the physiological motion of the subject;

for each of time points during the PET scan, determining a centroid of distribution (COD) of coincidence events in the target region at the time point based on the PET data;

generating, based on the COD corresponding to each of the time points, the physiological signal of the subject.

* * * * *